United States Patent [19]

Scarfone et al.

[11] Patent Number: 5,385,151
[45] Date of Patent: Jan. 31, 1995

[54] COAXIAL BONE MARROW BIOPSY NEEDLE ASSEMBLY

[75] Inventors: Frank A. Scarfone, Boca Raton; David Turkel, Miami, both of Fla.

[73] Assignee: Symbiosis Corporation, Miami, Fla.

[21] Appl. No.: 145,793

[22] Filed: Nov. 1, 1993

Related U.S. Application Data

[63] Continuation-in-part of Ser. No. 942,427, Sep. 9, 1992, Pat. No. 5,257,632.

[51] Int. Cl.⁶ ............................................. A61B 10/00
[52] U.S. Cl. .................................................... 128/754
[58] Field of Search ........................... 128/752-754; 604/27, 28, 35, 49, 51, 164, 165, 167, 264, 272, 280

[56] References Cited

U.S. PATENT DOCUMENTS

| | | | |
|---|---|---|---|
| 4,256,119 | 3/1981 | Gauthier | 128/754 |
| 4,258,722 | 3/1981 | Sessions et al. | 128/753 |
| 4,262,676 | 4/1981 | Jamshidi | 128/753 |
| 4,314,565 | 2/1982 | Lee | 128/753 |
| 4,356,828 | 11/1982 | Jamshidi | 128/754 |
| 4,403,617 | 9/1983 | Tretinyak | 128/753 |
| 4,469,109 | 9/1984 | Mehl | 128/753 |
| 4,487,209 | 12/1984 | Mehl | 128/754 |
| 4,513,754 | 4/1985 | Lee | 128/753 |
| 4,630,616 | 12/1986 | Tretinyak | 128/753 |
| 4,655,226 | 4/1987 | Lee | 128/754 |
| 4,793,363 | 12/1988 | Ausherman et al. | 128/754 |
| 4,838,282 | 6/1989 | Strasser et al. | 128/754 |

*Primary Examiner*—Max Hinderburg
*Attorney, Agent, or Firm*—David P. Gordon

[57] ABSTRACT

A coaxial bone marrow biopsy needle assembly is disclosed. The assembly includes a hollow cannula with a handle having an interlocking device and a trocar insertable in the cannula and having a second handle with another interlocking device which mates with the interlocking device in the cannula handle. The interlocking devices are a spring biased pin radially entering a receiving socket, and a notched projection which extends into the receiving socket. The pin has a ramped portion, and the notched projection has a rounded or conical tip which rides down the ramped portion of the pin and thereby pushes the biased pin radially out of the socket during assembly of the hollow cannula with the trocar. The assembled handles provides a smooth upper surface which fits comfortably in a palm and a lower gripping surface around which fingers easily wrap. The interlocking devices hold the handles securely together keeping the trocar within the cannula during puncture, but are easily separated thereafter.

20 Claims, 1 Drawing Sheet

COAXIAL BONE MARROW BIOPSY NEEDLE ASSEMBLY

This application is a continuation-in-part of application U.S. Ser. No. 07/942,427 filed Sep. 9, 1992 U.S. Pat. No. 5,257,632 and hereby incorporated by reference herein in its entirety.

BACKGROUND OF THE INVENTION

1. Field of the Invention

This invention relates to surgical biopsy needle instruments. More particularly, this invention relates to an interlocking handle arrangement for a coaxial bone marrow biopsy needle assembly.

2. State of the Art

Known biopsy needles generally include a cannula having a lumen extending therethrough, and a trocar or stylet which is removably inserted through the lumen of the cannula. The proximal ends of the cannula and trocar are provided with some type of gripping means and the distal ends of the cannula and trocar are sharpened to a bone piercing edge. In order to obtain a bone marrow specimen, the trocar and cannula are forced through the outer hard layer of the bone containing the marrow. Once the softer, internal region of the bone is reached, the trocar is withdrawn. A specimen is obtained either by advancing the cannula further into the bone to obtain a core sample, or by coupling a fluid conduit to the proximal end of the cannula and aspirating a liquid sample. When taking a core sample, the cannula containing the core sample of bone marrow is carefully withdrawn so as to retain the marrow material.

The bone marrow biopsy procedure is quite painful to the patient and requires much exertion by the physician. Early problems with biopsy needles involved the sharpness of the cannula and trocar and the gripping means used so that the needle could be placed accurately and the bone could be penetrated quickly. U.S. Pat. No. 4,356,828, for example, discloses an improved finger gripping member and U.S. Pat. No. 4,403,617 discloses particular cutting edge configurations for the trocar and cannula.

Developments in the gripping means of the trocar and cannula continued with emphasis placed on the secure engagement of the trocar within the cannula and ease of use for the physician. U.S. Pat. Nos. 4,922,602 to Mehl, 4,838,282 to Strasser et al., 4,793,363 to Ausherman et al., and 4,469,109 to Mehl, for example, disclose fairly elaborate interlocking systems between the trocar gripping means and the cannula gripping means and different shapes for the gripping means. The object in providing an interlocking system between the trocar and the cannula is to keep the trocar securely in the cannula while the instrument is being forced through the outer hard layer of bone. Strasser et al. shows a frictional engagement between the trocar handle and the cannula handle. This type of interlocking system is often either too loose to hold the handles together securely or too tight to allow easy separation of the handles when removing the trocar from the cannula. Mehl and Ausherman et al. show a pin and groove twist-locking system. Here, the trocar handle is aligned with the cannula handle in a first position, pushed closer to the cannula handle and then twisted relative to the cannula handle to lock the handles to each other. This type of interlocking system is almost always secure but it is also almost always difficult to unlock the handles from one another.

The previously incorporated parent of the instant application discloses a three part bone marrow biopsy needle assembly for obtaining a bone marrow core biopsy and a bone marrow aspirate biopsy in a single procedure. The needle assembly has an outer aspiration sheath which closely surrounds a coaxial inner hollow coring needle, and a trocar which extends through the coring needle. A handle arrangement is provided to allow insertion into the bone of the central trocar, the core biopsy needle and the outer aspiration sheath as an assembly, and to further allow stable manipulation of each component of the system without displacing the outer aspiration sheath. The handle arrangement is provided with a latching mechanism which prevents the trocar and aspiration cannula from being assembled together by themselves. The coring needle must inserted into the aspiration cannula and the coring handle attached to the aspiration handle before the trocar handle can be attached. Interlocking of the three handles is accomplished by a biased radial locking pin in the handle of the outer aspiration sheath which engages a notch in longitudinal projections extending from the handles of the coring needle and the trocar. This interlocking system overcomes the disadvantages of the frictional engagement systems and the twist-lock systems. The handles are held securely together but are easily separated from each other by the physician.

It has been recognized that, while it is often necessary to take both solid and liquid biopsy samples from the same site, it is sometimes only necessary to take a solid or a liquid sample. In those cases, the three part bone marrow biopsy needle assembly of the parent application can be used, but requires the otherwise unnecessary inclusion of both the coring needle and aspiration sheath in the assembly prior to insertion into the bone marrow and the removal of both the trocar and the coring needle prior to aspiration.

SUMMARY OF THE INVENTION

It is therefore an object of the invention to provide a two part bone marrow biopsy needle assembly having a handle arrangement which allows easy insertion and stable manipulation of the components of the needle assembly.

It is also an object of the invention to provide a two part bone marrow biopsy needle assembly having interlocking handles which are held securely together and are easily separated by the physician.

In accord with these objects which will be discussed in detail below, the bone marrow biopsy needle assembly of the present invention generally comprises an outer aspiration or coring cannula which closely surrounds a removable coaxial pointed metal trocar or stylet. Both the cannula and trocar include a handle. The handle arrangement is provided to allow an easy insertion of the trocar and outer cannula assembly into the bone, and to further allow stable manipulation and removal of the trocar without displacing the outer cannula. The handles interlock by providing the cannula handle with a radially biased pin and by providing the trocar handle with a ramped and notched longitudinal projection. When the trocar is inserted into the cannula, the ramped portion of the longitudinal projection on the trocar handle enters the cannula handle and moves the radially biased pin radially against its bias. The handles are pressed together until the notched portion of the longitudinal projection aligns with the radially biased pin and the pin engages the notch. The handles are easily separated by pulling them apart.

Additional objects and advantages of the invention will become apparent to those skilled in the art upon reference to the detailed description taken in conjunction with the provided figures.

DETAILED DESCRIPTION OF THE PREFERRED EMBODIMENT

Figure 2:
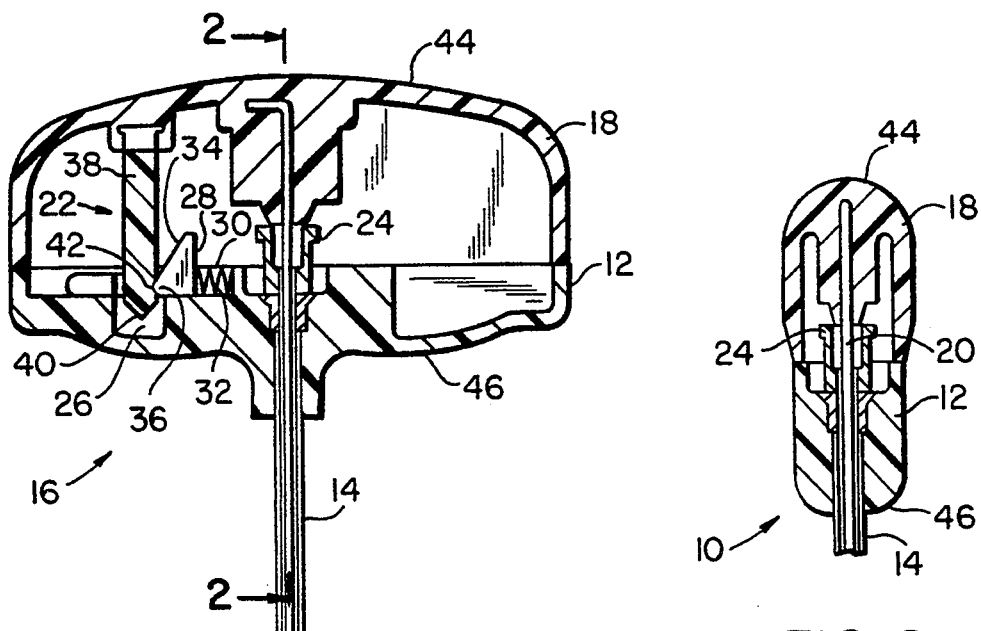
FIG. 2 is a cross section along line 2—2 of FIG. 1.
Figure 1:
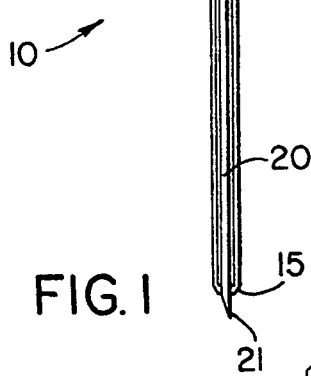
FIG. 1 is an assembled cross sectional view of a two part bone marrow biopsy needle assembly according to the invention.
Figure 3:
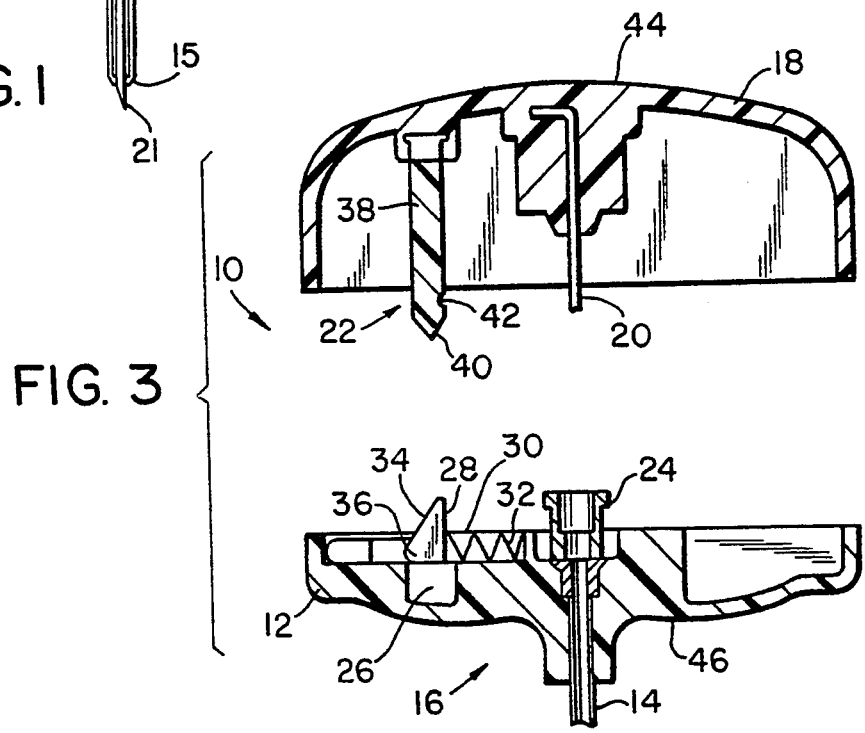
FIG. 3 is a view similar to FIG. 1, but exploded to show the separate cannula and trocar handles.

Referring now to FIGS. 1-3, the coaxial bone marrow biopsy needle assembly 10 includes a plastic cannula handle 12 carrying a metal cannula 14 and a latching mechanism 16. A plastic trocar handle 18 carrying a metal trocar 20 and a latching device 22 couples with the cannula handle 12 as shown in FIGS. 1 and 2 when the trocar 20 is fully inserted into the cannula 14. Those skilled in the art will appreciate that when the trocar 20 is fully inserted into the cannula 14, the sharp distal end 21 of the trocar 20 extends beyond the distal end 15 of the cannula 14. It will also be appreciated that the outer surface of the distal end 15 of the cannula 14 is typically tapered radially inward thereby forming a relatively smooth transition from the sharp distal end 21 of trocar 20 to the smooth cylindrical surface of the cannula 14.

Cannula 14 may be an aspiration cannula, a coring cannula, or a dual purpose cannula and it is preferably insert molded in the cannula handle 12. When used for coring, the cannula 14 is advantageously provided with internal threading as shown in the parent application. When used for aspiration, the cannula 14 is provided with a proximal luer connection 24 which may be molded as an integral part of the cannula handle 12.

The latching device 22 in the cannula handle 12 includes a receiving socket 26 having a longitudinal axis substantially parallel to and radially spaced apart from the longitudinal axis of the cannula 14. A sliding pin 28 is mounted in a slot 30 which extends radially into the receiving socket 26. A biasing spring 32 in the slot 30 biases the sliding pin 28 radially into the receiving socket 26. The end of the sliding pin 28 which enters the receiving socket 26 is provided with a rounded tip 36 and an upper ramped portion 34.

Trocar 20 is preferably insert molded in trocar handle 18 and has an outer diameter slightly smaller than the inner diameter of the cannula 14. The latching device 22 in the trocar handle 18 includes a stationary pin 38 having a rounded or conical tip 40 and a radial notch 42. The stationary pin 38 has a longitudinal axis substantially parallel to and radially spaced apart from the longitudinal axis of the trocar 20 and an outer diameter slightly smaller than the inner diameter of the receiving socket 26 in the cannula handle 12. As will be appreciated, the radial distance between the longitudinal axes of the stationary pin 38 and the trocar 20 is substantially the same as the radial distance between the longitudinal axes of the cannula 14 and the receiving socket 26 in the cannula handle 12. The stationary pin 38 may be metal and insert molded in the trocar handle 18 or may be plastic and molded as an integral part of the plastic trocar handle 18. As seen best in FIG. 1, the stationary pin 38 extends for a length such that it enters the receiving socket 26 in the cannula handle 12 when the trocar 20 is fully inserted in the cannula 14. The radial notch 42 on the stationary pin 38 is located such that it is engaged by the rounded end 36 of the sliding pin 28 when the trocar 20 is fully inserted into the cannula 14 as shown in FIG. 1.

Those skilled in the art will appreciate that when the trocar 20 is inserted into the cannula 14, the rounded or conical tip 40 of the stationary pin 38 will contact the ramped portion 34 of the sliding pin 28 before the trocar is fully inserted into the cannula. This pushes the sliding pin 28 back against spring 32 clearing the entry to the socket 26. As the stationary pin 38 enters the socket 26, the radial notch 42 comes into closer alignment with the rounded tip 36 of the sliding pin 28. When the trocar 20 is fully inserted into the cannula 14 and the handles 12 and 18 are in close contact as shown in FIG. 1, the radial notch 42 in the stationary pin 38 is radially aligned with the rounded tip 36 of sliding pin 28. In this position, spring 32 biases the sliding pin 28 so that the rounded tip 36 enters and engages the radial notch 42. The engagement of the rounded tip 36 of the sliding pin 28 with the radial notch 42 of the stationary pin 38 holds the handles 12 and 18 in close contact as shown in FIG. 1. When assembled as shown in FIG. 1, the handle 18 presents a smooth upper surface 44 which rests comfortably in the physician's palm and the handle 12 presents a lower curved gripping surface 46 against which the physician's fingers grip. Those skilled in the art will appreciate that after the needle assembly is inserted into the bone, the trocar 20 and trocar handle 18 may be easily removed from the cannula 14 and cannula handle 12 by gently pulling the trocar handle 18 away from the cannula handle 12 so that the rounded tip 36 of the sliding pin 28 pops out of the radial notch 42 in the stationary pin 38.

There has been described and illustrated herein a coaxially disposed bone marrow biopsy needle assembly with interlocking handles. While a preferred embodiment of the invention has been described, it is not intended that the invention be limited thereto, as it is intended that the invention be as broad in scope as the art will allow and that the specification be read likewise. Thus, while the trocar handle has been disclosed as having a stationary pin with a radial notch and the cannula handle has been disclosed as having a radially biased pin for engaging the notch, it will be appreciated that the relative locations of these pins could be reversed. The radially biased pin could be provided on the trocar handle while the stationary pin with radial notch could be provided on the cannula handle. Moreover, the radial notch may be configured in several ways as those skilled in the art will appreciate. It may surround the circumference of the stationary pin or may cover only a portion of the circumference of the stationary pin. In addition, while the biased latching pin has been shown as being biased radially outward, it will be appreciated that the latching pin may be biased in other directions and still achieve substantially the same result in substantially the same manner as described herein. Also, while the trocar handle and cannula handle have been disclosed as being constructed of plastic, it will be recognized that other types of material could be used with similar results obtained. Moreover, while particular configurations have been disclosed in reference to the ergonomic shapes of the handles, it will be appreciated that other configurations could be used as well. Furthermore, while the cannula has been disclosed as having a proximal luer connection, it will be understood that different types of fluid couplings can achieve the same or similar function as disclosed herein. Therefore, it will be appreciated by those skilled in the art that modifications could be made to the provided invention without deviating from its spirit and scope as so claimed.

We claim:

1. A bone marrow biopsy needle assembly, comprising:
   a) a cannula assembly having a hollow cannula with a distal tip, and a first handle which receives and surrounds a proximal portion of said hollow cannula at a proximal portion thereof; and
   b) a trocar assembly having a trocar having a distal tip, and a second handle which receives a proximal portion of said trocar, said second handle being proximal said first handle, said trocar extending substantially coaxially through said hollow aspiration cannula with said distal tip of said trocar extending distally past said distal tip of said hollow cannula, said trocar being removable from said hollow cannula, wherein
   said first handle has first mating means for mating with said second handle and said second handle has second mating means for mating with said first handle, and
   one of said first mating means and said second mating means includes a spring biased latch means for latching, and the other of said first mating means and said second mating means includes a latch engaging catch means for receiving said spring biased latch means.

2. A bone marrow biopsy needle assembly according to claim 1, wherein:
   said spring biased latch means includes a receiving socket, and said latch engaging catch means comprises a first projection extending into said receiving socket.

3. A bone marrow biopsy needle assembly according to claim 2, wherein:
   said first handle has said latch means including said receiving socket, and said second handle has said first projection.

4. A bone marrow biopsy needle assembly according to claim 1, wherein:
   said spring biased latch means comprises a slot in said first proximal handle, a spring in said slot, and a pin biased by said spring in said slot, said pin means being biased radially outward with respect to a longitudinal axis of said hollow aspiration cannula, and
   said latch engaging catch means extends into said slot and is disengageably mated by said pin.

5. A bone marrow biopsy needle assembly according to claim 4, wherein:
   said radially biased pin includes a ramped portion, and said latch engaging catch means rides down said ramped portion of said pin means and thereby pushes said biased pin radially inward during assembly of said hollow cannula with said trocar.

6. A bone marrow biopsy needle assembly according to claim 1, wherein:
   said first handle includes a distal surface having indentations around which fingers of a practitioner are easily wrapped, and said second handle includes a smooth proximal surface which fits comfortably in a palm of the practitioner.

7. A bone marrow biopsy needle assembly, comprising:
   a) a hollow cannula having a proximal and a distal end;
   b) a cannula handle coupled to said proximal end of said cannula;
   c) a trocar having a proximal and a distal end and being removably insertable into said hollow cannula; and
   d) a trocar handle coupled to said proximal end of said trocar,
   said cannula handle having a first interlocking means for coupling said cannula handle to said trocar handle, and said trocar handle having a second interlocking means for coupling said trocar handle to said cannula handle, one of said first and second interlocking means being spring biased.

8. A bone marrow biopsy needle assembly according to claim 7, wherein:
   said spring biased interlocking means comprises a socket and a spring biased pin radially entering said socket.

9. A bone marrow biopsy needle assembly according to claim 8, wherein:
   the other of said first and second locking means comprises a notched projection which enters said socket and is engaged by said spring biased pin.

10. A bone marrow biopsy needle assembly according to claim 9, wherein:
    said spring biased pin has a ramped portion which is engaged by said notched projection as said notched projection enters said socket.

11. A bone marrow biopsy needle assembly according to claim 10, wherein:
    said notched projection has a tapered tip.

12. A bone marrow biopsy needle assembly according to claim 11, wherein:
    said first interlocking means is spring biased.

13. A bone marrow biopsy needle assembly according to claim 8, wherein:
    said pin has a rounded end entering said socket.

14. A bone marrow biopsy needle assembly according to claim 7, further comprising:
    e) a fluid coupling coupled to said proximal end of said hollow cannula for coupling a fluid conduit to said cannula.

15. A bone marrow biopsy needle assembly according to claim 14, wherein:
    said fluid coupling is an integral part of said cannula handle.

16. A bone marrow biopsy needle assembly according to claim 15, wherein:
    said fluid coupling is a luer connector.

17. A bone marrow biopsy needle assembly according to claim 7, wherein:
    said trocar handle has a rounded palm receiving upper surface and said cannula handle has a rounded finger receiving lower surface.

18. A bone marrow biopsy needle assembly according to claim 7, wherein:
    said trocar handle is plastic and said trocar is insert molded in said plastic trocar handle; and said cannula handle is plastic and said hollow cannula is insert molded in said cannula handle.

19. A bone marrow biopsy needle assembly according to claim 7, wherein:
   the other of said first and second interlocking means is formed as an integral part of a respective one of said cannula handle and said trocar handle.

20. A bone marrow biopsy needle assembly according to claim 7, wherein:
   the other of said first and second interlocking means is insert molded in a respective one of said cannula handle and said trocar handle.

* * * * *